(12) United States Patent
Bavendiek et al.

(10) Patent No.: US 7,522,700 B2
(45) Date of Patent: Apr. 21, 2009

(54) METHOD FOR AUTOMATIC DEFECT RECOGNITION IN TESTPIECES BY MEANS OF AN X-RAY EXAMINATION UNIT

(75) Inventors: Klaus Bavendiek, Norderstedt (DE); Frank Herold, Ahrensburg (DE)

(73) Assignee: Yxlon International X-Ray GmbH, Hamburg (DE)

( * ) Notice: Subject to any disclaimer, the term of this patent is extended or adjusted under 35 U.S.C. 154(b) by 157 days.

(21) Appl. No.: 11/414,588

(22) Filed: Apr. 28, 2006

(65) Prior Publication Data

US 2006/0245542 A1    Nov. 2, 2006

(30) Foreign Application Priority Data

Apr. 29, 2005    (DE) ................... 10 2005 020 149

(51) Int. Cl.
*G01N 23/18* (2006.01)
(52) U.S. Cl. ........................................ 378/58; 378/205
(58) Field of Classification Search ............... 378/34, 378/58, 205
See application file for complete search history.

(56) References Cited

U.S. PATENT DOCUMENTS

| | | | | |
|---|---|---|---|---|
| 4,415,980 A | * | 11/1983 | Buchanan | 378/58 |
| 4,852,131 A | * | 7/1989 | Armistead | 378/4 |
| 5,199,054 A | * | 3/1993 | Adams et al. | 378/21 |
| 5,687,209 A | * | 11/1997 | Adams | 378/58 |
| 6,393,095 B1 | * | 5/2002 | Robinson | 378/58 |
| 6,937,753 B1 | * | 8/2005 | O'Dell et al. | 382/141 |
| 2002/0090057 A1 | * | 7/2002 | Sykes et al. | 378/205 |
| 2003/0039332 A1 | | 2/2003 | Bavendiek et al. | |
| 2004/0081281 A1 | | 4/2004 | Fadler et al. | |

FOREIGN PATENT DOCUMENTS

| | | |
|---|---|---|
| DE | 3113440 | 11/1982 |
| DE | 4202113 | 7/1993 |
| EP | 1148333 A1 | 10/2001 |
| EP | 1191827 A2 | 3/2002 |

OTHER PUBLICATIONS

European Search Report for parallel EP Application No. 06009093.3 dated Apr. 24, 2007.
Marek Karolczak et al, "Implementation of a cone-beam reconstruction algorithm for the single-circle source orbit with embedded misalignment correction using homogeneous coordinates", Medical Physics, Oct. 2001, 2050-2069, vol. 10, AIP, Melville, NY, USA.

* cited by examiner

*Primary Examiner*—Chih-Cheng G Kao
(74) *Attorney, Agent, or Firm*—Graybeal Jackson LLP

(57) ABSTRACT

A method for automatic defect recognition in testpieces by means of an X-ray examination unit having a mechanical manipulator for positioning the testpiece in a beam path of the X-ray examination unit, wherein a positioning image of the testpiece is compared with an ideal reference image. An axis of rotation, an angle of rotation and a displacement vector are calculated in order to arrive at an exact congruence of the positioning image of the testpiece with the ideal reference image. The values of the axis of rotation, angle of rotation and displacement vector are then relayed to the mechanical manipulator and the latter then transfers the testpiece into the position corresponding to these values.

10 Claims, No Drawings

METHOD FOR AUTOMATIC DEFECT RECOGNITION IN TESTPIECES BY MEANS OF AN X-RAY EXAMINATION UNIT

CROSS-REFERENCE TO RELATED APPLICATION

This is a utility application that claims foreign priority benefits under 35 USC §119 (a) to German Patent Application No. DE 10 2005 020 149.0, filed 29 Apr. 2005, which application is incorporated herein by reference.

BACKGROUND OF INVENTION

The invention relates to a method for automatic defect recognition in testpieces by means of an X-ray examination unit with an X-ray tube, a detector and a mechanical manipulator for positioning the testpiece in the beam path of the X-ray examination unit, wherein a positioning image of the testpiece is compared with an ideal reference image.

In the automatic defect recognition of testpieces by means of non-destructive analysis, an X-ray image of the testpiece is compared with an X-ray image of a different defect-free testpiece which serves as X-ray reference image. The decision whether a defective testpiece is present or not is reached solely on the basis of the automatic comparison between this X-ray reference image and the X-ray image of the testpiece without human involvement. On the one hand, each defective testpiece must necessarily be recognized, but on the other hand there should be as few as possible incorrect detections—in which testpieces that are actually defect-free are recognized as defective because the image of the testpiece deviates too markedly from the reference image.

Such incorrect detections often occur in the case of inaccuracies in the positioning of the testpiece, with the result that the comparison image produced of the latter has been displaced and/or twisted vis-à-vis the reference image. Due to the many degrees of freedom in positioning the testpiece in the X-ray examination unit, this is the rule rather than the exception. If for example a robot is used to grip and position the testpiece, there are already six degrees of freedom just in the gripping of the testpiece. If a pallet system is used, there are likewise six degrees of freedom with regard to the positional tolerance of the testpiece on the pallet due to natural testpiece tolerance (translation in three directions and rotation about each axis of translation); but to a much lesser extent than when gripping. In the case of a geared unit there are three degrees of freedom due to the conveyance and manipulator tolerance. Added to these in each case are also the component tolerances from production.

To date, this problem has been solved by using distinctive points in each case in the comparison image of the testpiece and of the reference image to match—regularly shift—the image processing regions. However, only three degrees of freedom can be corrected in this case and, because of the reliance on only a few distinctive points in the comparison image and in the reference image, it is also optimum only for these distinctive points in the comparison image. This is because in a two-dimensional image, in principle only the translation in two directions and the rotation on the plane are corrected, because otherwise there may be a significant loss of image information. Otherwise, three-dimensional information about the testpiece would have to be available. At the other points a greater deviation can occur between the comparison image and the reference image, which usually leads to a high proportion of incorrect detections.

Another method practised to date consists of pixel-by-pixel correction of the inaccuracy in positioning vis-à-vis the reference image through a similarity transformation between the reference image and the comparison image of the testpiece. Such a method involves a great deal of computation. Although a correction is carried out over the whole comparison image in this case, deviations from the set value can still occur which restrict the recognizability of defects.

SUMMARY OF INVENTION

The object of the invention is therefore to provide a more reliable method for automatic defect recognition with fewer incorrect detections than with the known methods.

The object is achieved by a method with the features of claim 1. After precisely calculating about what axis of rotation and at what angle of rotation the positioning image of the testpiece must be turned and by what displacement vector it must be shifted in order to arrive at an exact congruence with the reference image, these values are not—as in the state of the art—used to convert the positioning image to the coordinates of the reference image and then to carry out a comparison analysis. Rather, it is provided according to the invention that these obtained values (of the axis of rotation, angle of rotation and displacement vector) are relayed to the mechanical manipulator. The mechanical manipulator then transfers the testpiece into the corresponding position. In this position, a comparison image of the testpiece is produced in the X-ray examination unit. This comparison image is then congruent within the framework of the testpiece tolerances with an X-ray reference image which belongs to the ideal reference image of a defect-free testpiece. The thus recorded comparison image can then, without any conversion—as was necessary to date in the state of the art—be compared with the X-ray reference image of the defect-free testpiece using a known image processing system. As the image processing is not a subject of the invention, but merely a downstream factor and sufficiently known from the state of the art, it will not be examined in more detail here. Through the method according to the invention, an extremely precise positioning of the testpiece is possible, as the mechanics can achieve the desired position with a high degree of accuracy. As there is then, as stated above, an optimum congruence between the comparison image of the testpiece and the X-ray reference image, there are mainly detections due to material defects and testpiece tolerances and only a minimal number of incorrect detections due to shortcomings in the geometric alignment of the testpiece.

An advantageous development of the invention provides that the X-ray reference image and the ideal reference image constitute a coincident X-ray image of a defect-free testpiece. As in this case both the X-ray reference image and the ideal reference image are X-ray images, two different reference images of a defect-free testpiece need not be taken. As the positioning image of the testpiece is likewise an X-ray image, the examination of the position of the testpiece can be carried out inside the X-ray examination unit. As a result it is not necessary to provide an additional device outside the X-ray examination unit to record the positioning image of the testpiece and make available an ideal reference image corresponding to same in addition to the X-ray reference image of the defect-free testpiece. However, this reduced outlay is at the cost of an increased residence time of the testpiece inside the X-ray examination unit and thus a lower throughput, as an additional image feed with subsequent evaluation and calculation of the modification parameters and also the mechanical correction are necessary. This extra time is required for each testpiece.

Another advantageous development of the invention provides that the positioning image is obtained, like the ideal reference image, by means of visible light or X-radiation. As a result, the low throughput just described can be increased, as the position of the testpiece can already be recorded outside the X-ray examination unit. This can take place using image processing by means of lights and a stereoscopic camera technique. As this can take place in parallel with the examination of the testpiece inside the X-ray examination unit, a significant time saving and thus a higher throughput of testpieces is made possible. With the help of a suitable pattern—be it for example solid by means of material deposition, material removal or a stamping procedure, or virtual using lights—the otherwise error-prone search for correspondence using stereoscopy—according to the state of the art—is efficiently and robustly solved for the method according to the invention under real-time conditions. In this case, the measurement of the deviation between the positioning image of the testpiece and the ideal reference image is relayed to the mechanical manipulator which then automatically, when positioning the testpiece within the X-ray examination unit, brings the testpiece to the predetermined point with the calculated parameters for the congruent transfer, with the result that the recording of the comparison image of the testpiece essential to the invention can then take place, the position of the comparison image overlapping in optimum manner with the X-ray reference image of the defect-free testpiece.

It is particularly advantageous if a gripping arm which receives the calculated values for the axis of rotation, the angle of rotation and the displacement vector via appropriate control commands is used as mechanical manipulator. Such robots are well known from the state of the art and can be operated with a high degree of precision in respect of their positioning. Thus, apart from testpiece tolerances, an almost hundred percent congruence between the comparison image of the testpiece and the X-ray reference image of the defect-free testpiece is achieved.

In summary, it can be stated that through a method according to the invention—which differs fundamentally from the automatic defect recognition methods practised to date—the number of incorrect detections can be dramatically reduced, as there is no longer a need for a "virtual" position correction of the X-ray image of the testpiece taken in the X-ray examination unit at one angle or possibly at different angles and under slightly to significantly modified conditions. Rather, here the position of the testpiece is corrected mechanically, with the result that its comparison image, apart from natural testpiece tolerances, corresponds almost 100% to the X-ray reference image of the defect-free testpiece in respect of the screening angles and positioning. It is thereby possible to carry out very simple image processing with defect recognition following the invention.

What is claimed:

1. Method for automatic defect recognition in testpieces by means of an X-ray examination unit with an X-ray tube, a detector and a mechanical manipulator for positioning testpieces in a beam path of the X-ray examination unit, wherein a positioning image of a testpiece is compared with an ideal reference image,
   characterized in that
   values of an axis of rotation, an angle of rotation and a displacement vector are calculated in order to arrive at an exact congruence between the positioning image of the testpiece and the ideal reference image,
   the values of the axis of rotation, angle of rotation and displacement vector are relayed to the mechanical manipulator, which transfers the testpiece into a position corresponding to these values,
   whereby in this position, a comparison image of the testpiece, which serves for comparison with an X-ray reference image, is produced by the X-ray examination unit.

2. Method according to claim 1, characterized in that the X-ray reference image and the ideal reference image are one and the same coincident X-ray image of a defect-free testpiece and the positioning image is an X-ray image.

3. Method according to claim 1, characterized in that the positioning image is obtained, like the ideal reference image, by means of visible light.

4. Method according to claim 3, characterized in that the positioning image is recorded by means of lights and a stereoscopic camera technique.

5. Method according to claim 1, characterized in that the ideal reference image and the positioning image of the testpiece are compared with each other while another testpiece is examined in the X-ray examination unit.

6. Method according to claim 1, characterized in that the mechanical manipulator comprises a gripping arm, which receives the calculated values for the axis of rotation, the angle of rotation and the displacement vector via control commands.

7. Method according to claim 2, characterized in that the ideal reference image and the positioning image of the testpiece are compared with each other while another testpiece is examined in the X-ray examination unit.

8. Method according to claim 3, characterized in that the ideal reference image and the positioning image of the testpiece are compared with each other while another testpiece is examined in the X-ray examination unit.

9. Method according to claim 4, characterized in that the ideal reference image and the positioning image of the testpiece are compared with each other while another testpiece is examined in the X-ray examination unit.

10. Method according to claim 6, characterized in that the ideal reference image and the positioning image of the testpiece are compared with each other while another testpiece is examined in the X-ray examination unit.

* * * * *